(12) United States Patent
Balasubramaniam et al.

(10) Patent No.: US 7,344,991 B2
(45) Date of Patent: Mar. 18, 2008

(54) METHOD AND APPARATUS FOR MULTILAYER PHOTORESIST DRY DEVELOPMENT

(75) Inventors: Vaidyanathan Balasubramaniam, Beverly, MA (US); Koichiro Inazawa, Peabody, MA (US); Rich Wise, New Windsor, NY (US); Arpan Mahorowala, Bronxville, NY (US); Siddhartha Panda, Beacon, NY (US)

(73) Assignee: Tokyo Electron Limited (JP)

( * ) Notice: Subject to any disclaimer, the term of this patent is extended or adjusted under 35 U.S.C. 154(b) by 0 days.

(21) Appl. No.: 10/640,577

(22) Filed: Aug. 14, 2003

(65) Prior Publication Data

US 2004/0180269 A1 Sep. 16, 2004

Related U.S. Application Data

(60) Provisional application No. 60/458,430, filed on Mar. 31, 2003, provisional application No. 60/484,225, filed on May 5, 2003, provisional application No. 60/435,286, filed on Dec. 23, 2002.

(51) Int. Cl.
*H01L 21/461* (2006.01)
*H01L 21/302* (2006.01)

(52) U.S. Cl. ............ 438/706; 438/710; 438/717; 438/725; 438/734

(58) Field of Classification Search ............ None
See application file for complete search history.

(56) References Cited

U.S. PATENT DOCUMENTS 5,656,128 A * 8/1997 Hashimoto et al. ........... 216/47
5,773,199 A * 6/1998 Linliu et al. ............... 430/316
6,039,888 A * 3/2000 Ha et al. ..................... 216/13
6,080,529 A * 6/2000 Ye et al. ..................... 430/318
6,080,678 A * 6/2000 Yim .............................. 438/725
6,143,476 A 11/2000 Ye et al.

(Continued)

FOREIGN PATENT DOCUMENTS

EP 0 517 165 A1 12/1992

(Continued)

OTHER PUBLICATIONS

Rossnagel et al., Handbook of Plasma Processing, 1990, Noyes Publications, pp. 203-205.*

(Continued)

*Primary Examiner*—Duy-Vu N Deo

(57) ABSTRACT

A method for etching an organic anti-reflective coating (ARC) layer on a substrate in a plasma processing system comprising: introducing a process gas comprising ammonia ($NH_3$), and a passivation gas; forming a plasma from the process gas; and exposing the substrate to the plasma. The process gas can, for example, constitute $NH_3$ and a hydrocarbon gas such as at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, and $C_6H_{12}$. Additionally, the process chemistry can further comprise the addition of helium. The present invention further presents a method for forming a bilayer mask for etching a thin film on a substrate, wherein the method comprises: forming the thin film on the substrate; forming an ARC layer on the thin film; forming a photoresist pattern on the ARC layer; and transferring the photoresist pattern to the ARC layer with an etch process using a process gas comprising ammonia ($NH_3$), and a passivation gas.

7 Claims, 9 Drawing Sheets

U.S. PATENT DOCUMENTS

| | | |
|---|---|---|
| 6,352,937 B1 | 3/2002 | Kadomura et al. |
| 6,458,516 B1 * | 10/2002 | Ye et al. ............... 430/317 |
| 6,617,257 B2 * | 9/2003 | Ni et al. ............... 438/725 |
| 2002/0111036 A1 | 8/2002 | Zhu et al. |
| 2002/0173160 A1 | 11/2002 | Keil et al. |
| 2003/0029835 A1 | 2/2003 | Yauw et al. |
| 2004/0092098 A1 * | 5/2004 | Sudijono et al. ........... 438/637 |
| 2004/0185380 A1 * | 9/2004 | Igarashi et al. ............ 430/313 |

FOREIGN PATENT DOCUMENTS

| | | |
|---|---|---|
| EP | 0 813 233 A2 | 12/1997 |
| WO | WO 00/51173 | 8/2000 |
| WO | WO 03/030237 A1 | 4/2003 |

OTHER PUBLICATIONS

Wold, Silicon Processing for the VLSI Era, 2002, Lattice Press, vol. 4, p. 248.*

Wolf et al., Silicon Processing for the VLSI Era, 1986, Lattice Press, vol. 1, pp. 565, 567.*

* cited by examiner

METHOD AND APPARATUS FOR MULTILAYER PHOTORESIST DRY DEVELOPMENT

CROSS-REFERENCE TO RELATED APPLICATIONS

This application is related to and claims priority to U.S. provisional application Ser. No. 60/458,430 filed on Mar. 31, 2003, and U.S. provisional application Ser. No. 60/484,225 filed on May 5, 2003; the entire contents of which are herein incorporated by reference. This application is related to co-pending application 60/435,286, entitled "Method and Apparatus For Bilayer Photoresist Dry Development," filed on Dec. 23, 2002; the entire contents of which are herein incorporated by reference.

FIELD OF THE INVENTION

The present invention relates to a method and apparatus for plasma processing a substrate, and more particularly to a method for multilayer photoresist dry development.

BACKGROUND OF THE INVENTION

During semiconductor processing, a (dry) plasma etch process can be utilized to remove or etch material along fine lines or within vias or contacts patterned on a silicon substrate. The plasma etch process generally involves positioning a semiconductor substrate with an overlying patterned, protective layer, for example a photoresist layer, in a processing chamber. Once the substrate is positioned within the chamber, an ionizable, dissociative gas mixture is introduced within the chamber at a pre-specified flow rate, while a vacuum pump is throttled to achieve an ambient process pressure. Thereafter, a plasma is formed when a fraction of the gas species present are ionized by electrons heated via the transfer of radio frequency (RF) power either inductively or capacitively, or microwave power using, for example, electron cyclotron resonance (ECR). Moreover, the heated electrons serve to dissociate some species of the ambient gas species and create reactant specie(s) suitable for the exposed surface etch chemistry. Once the plasma is formed, selected surfaces of the substrate are etched by the plasma. The process is adjusted to achieve appropriate conditions, including an appropriate concentration of desirable reactant and ion populations to etch various features (e.g., trenches, vias, contacts, etc.) in the selected regions of the substrate. Such substrate materials where etching is required include silicon dioxide ($SiO_2$), low-k dielectric materials, polysilicon, and silicon nitride.

SUMMARY OF THE INVENTION

The present invention relates to a method and apparatus for plasma processing a substrate, and to a method and apparatus for multilayer photoresist dry development. The present invention also relates to the multilayer mask itself.

In one aspect of the invention, a method and apparatus are described for etching an anti-reflective coating (ARC) layer on a substrate in a plasma processing system. A process gas comprising one or more gasses collectively containing ammonia ($NH_3$) and a passivation gas is introduced. A plasma is formed from the process gas in the plasma processing system. The substrate is exposed to the plasma.

In yet another aspect of the invention, a method and apparatus are described for forming a bilayer mask for etching a thin film on a substrate. The thin film is formed on the substrate. An anti-reflective coating (ARC) layer is formed on the thin film. A photoresist pattern is formed on the ARC layer. The photoresist pattern is transferred to the ARC layer by etching the ARC layer using a process gas comprising one or more gasses collectively containing ammonia ($NH_3$) and a passivation gas.

Additionally, a method of smoothing a sidewall in a multilayer mask on a substrate in a plasma processing system comprises: introducing a process gas comprising one or more gasses collectively containing ammonia ($NH_3$), and a passivation gas; forming a plasma from the process gas in the plasma processing system; and exposing the substrate to the plasma, wherein the passivation gas facilitates the formation of a passivation film on the sidewall of the multilayer mask in order to smooth surface roughness of the sidewall.

DETAILED DESCRIPTION OF SEVERAL EMBODIMENTS

Figure 1A:
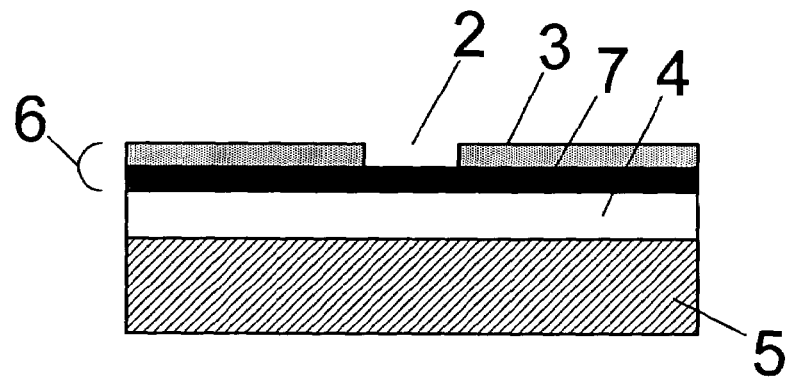
FIGS. 1A, 1B, and 1C show a schematic representation of a typical procedure for pattern etching a thin film.
Figure 1B:
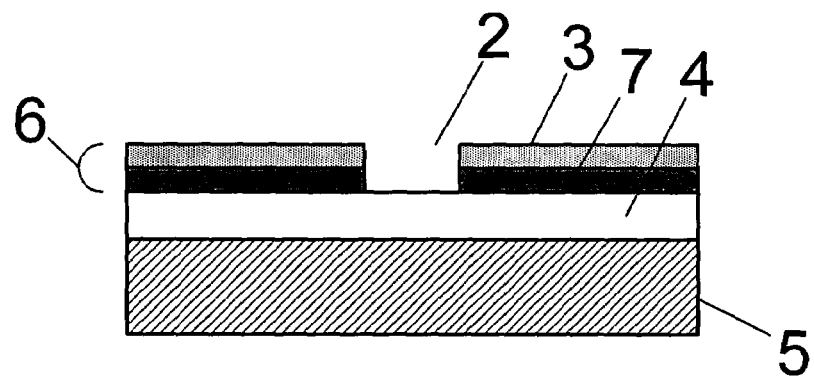
Figure 1C:
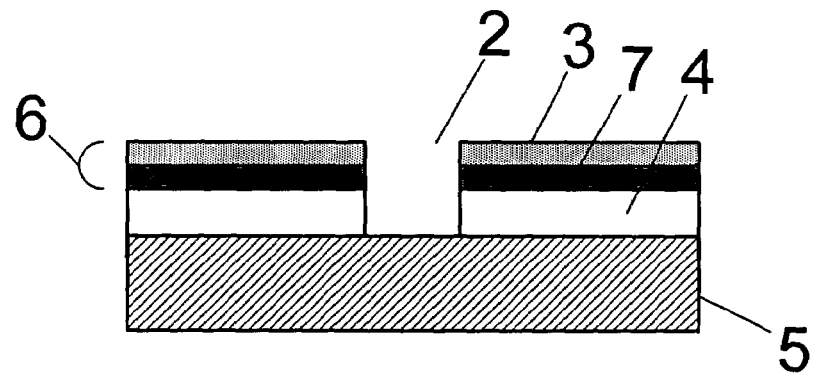

In material processing methodologies, pattern etching comprises the application of a thin layer of light-sensitive material, such as photoresist, to an upper surface of a substrate, that is subsequently patterned in order to provide a mask for transferring this pattern to the underlying thin film on a substrate during etching. The patterning of the light-sensitive material generally involves exposure by a radiation source through a reticle (and associated optics) of the light-sensitive material using, for example, a microlithography system, followed by the removal of the irradiated regions of the light-sensitive material (as in the case of positive photoresist), or non-irradiated regions (as in the case of negative resist) using a developing solvent. Multilayer masks can be implemented for etching features in a thin film. For example, as shown in FIGS. 1A-C, a bilayer mask 6 comprising light-sensitive layer 3 with pattern 2 formed using conventional lithographic techniques and an organic anti-reflective coating (ARC) layer 7 can be utilized as a mask for etching the thin film 4 on substrate 5, wherein the mask pattern 2 in the light-sensitive layer 3 is transferred to the ARC layer 7 using a separate etch step preceding the main etch step for the thin film 4.

In one embodiment, a process gas comprising ammonia ($NH_3$) and a passivation gas is utilized in a method of bilayer photoresist dry development. For example, the passivation gas can comprise a hydrocarbon gas such as at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, $C_6H_{12}$, or the like.

Although the embodiment above describes the etching of thin film 4 on substrate 5, the etching can be of substrate 5 itself, with or without thin film 4.

Figure 2:
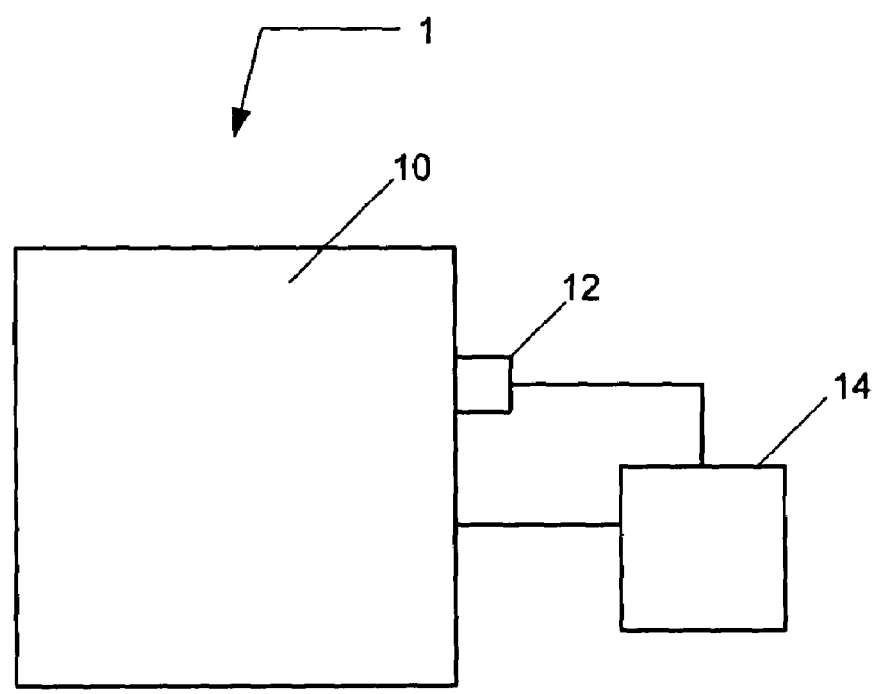
FIG. 2 shows a simplified schematic diagram of a plasma processing system according to an embodiment of the present invention.

According to one embodiment, a plasma processing system 1 is depicted in FIG. 2 comprising a plasma processing chamber 10, a diagnostic system 12 coupled to the plasma processing chamber 10, and a controller 14 coupled to the diagnostic system 12 and the plasma processing chamber 10. The controller 14 is configured to execute a process recipe comprising at least one of the above-identified chemistries to etch an organic ARC layer. Additionally, controller 14 is configured to receive at least one endpoint signal from the diagnostic system 12 and to post-process the at least one endpoint signal in order to accurately determine an endpoint for the process. In the illustrated embodiment, plasma processing system 1, depicted in FIG. 2, utilizes a plasma for material processing. Plasma processing system 1 can comprise an etch chamber.

Figure 3:
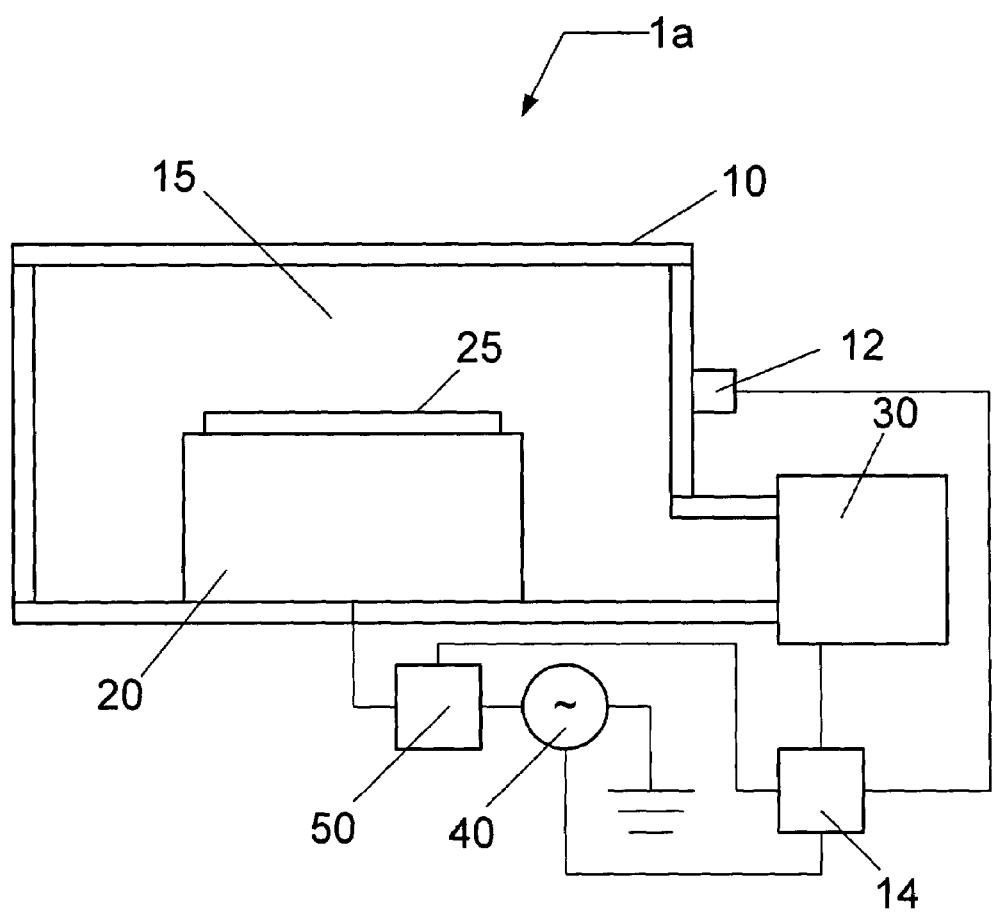
FIG. 3 shows a schematic diagram of a plasma processing system according to another embodiment of the present invention.

According to the embodiment depicted in FIG. 3, plasma processing system 1a can comprise plasma processing chamber 10, substrate holder 20, upon which a substrate 25 to be processed is affixed, and vacuum pumping system 30. Substrate 25 can be, for example, a semiconductor substrate, a wafer or a liquid crystal display. Plasma processing chamber 10 can be, for example, configured to facilitate the generation of plasma in processing region 15 adjacent a surface of substrate 25. An ionizable gas or mixture of gases is introduced via a gas injection system (not shown) and the process pressure is adjusted. For example, a control mechanism (not shown) can be used to throttle the vacuum pumping system 30. Plasma can be utilized to create materials specific to a pre-determined materials process, and/or to aid the removal of material from the exposed surfaces of substrate 25. The plasma processing system 1a can be configured to process 200 mm substrates, 300 mm substrates, or larger.

Substrate 25 can be, for example, affixed to the substrate holder 20 via an electrostatic clamping system. Furthermore, substrate holder 20 can, for example, further include a cooling system including a re-circulating coolant flow that receives heat from substrate holder 20 and transfers heat to a heat exchanger system (not shown), or when heating, transfers heat from the heat exchanger system. Moreover, gas can, for example, be delivered to the back-side of substrate 25 via a backside gas system to improve the gas-gap thermal conductance between substrate 25 and substrate holder 20. Such a system can be utilized when temperature control of the substrate is required at elevated or reduced temperatures. For example, the backside gas system can comprise a two-zone gas distribution system, wherein the helium gas gap pressure can be independently varied between the center and the edge of substrate 25. In other embodiments, heating/cooling elements, such as resistive heating elements, or thermoelectric heaters/coolers can be included in the substrate holder 20, as well as the chamber wall of the plasma processing chamber 10 and any other component within the plasma processing system 1a.

In the embodiment shown in FIG. 3, substrate holder 20 can comprise an electrode through which RF power is coupled to the processing plasma in process space 15. For example, substrate holder 20 can be electrically biased at a RF voltage via the transmission of RF power from a RF generator 40 through an impedance match network 50 to substrate holder 20. The RF bias can serve to heat electrons to form and maintain plasma. In this configuration, the system can operate as a reactive ion etch (RIE) reactor, wherein the chamber and an upper gas injection electrode serve as ground surfaces. A typical frequency for the RF bias can range from 0.1 MHz to 100 MHz. RF systems for plasma processing are well known to those skilled in the art.

Alternately, RF power is applied to the substrate holder electrode at multiple frequencies. Furthermore, impedance match network 50 serves to improve the transfer of RF power to plasma in plasma processing chamber 10 by reducing the reflected power. Match network topologies (e.g. L-type, π-type, T-type, etc.) and automatic control methods are well known to those skilled in the art.

Vacuum pump system 30 can, for example, include a turbo-molecular vacuum pump (TMP) capable of a pumping speed up to 5000 liters per second (and greater) and a gate valve for throttling the chamber pressure. In conventional plasma processing devices utilized for dry plasma etch, a 1000 to 3000 liter per second TMP is generally employed. TMPs are useful for low pressure processing, typically less than 50 mTorr. For high pressure processing (i.e., greater than 100 mTorr), a mechanical booster pump and dry roughing pump can be used. Furthermore, a device for monitoring chamber pressure (not shown) can be coupled to the plasma processing chamber 10. The pressure measuring device can be, for example, a Type 628B Baratron absolute capacitance manometer commercially available from MKS Instruments, Inc. (Andover, Mass.).

Controller 14 comprises a microprocessor, memory, and a digital I/O port capable of generating control voltages sufficient to communicate and activate inputs to plasma processing system 1a as well as monitor outputs from plasma processing system 1a. Moreover, controller 14 can be coupled to and can exchange information with RF generator 40, impedance match network 50, the gas injection system (not shown), vacuum pump system 30, as well as the backside gas delivery system (not shown), the substrate/substrate holder temperature measurement system (not shown), and/or the electrostatic clamping system (not shown). For example, a program stored in the memory can be utilized to activate the inputs to the aforementioned components of plasma processing system 1a according to a process recipe in order to perform the method of etching an organic ARC layer. One example of controller 14 is a DELL PRECISION WORKSTATION 610™, available from Dell Corporation, Austin, Tex.

The diagnostic system 12 can include an optical diagnostic subsystem (not shown). The optical diagnostic subsystem can comprise a detector such as a (silicon) photodiode or a photomultiplier tube (PMT) for measuring the light intensity emitted from the plasma. The diagnostic system 12 can further include an optical filter such as a narrow-band interference filter. In an alternate embodiment, the diagnostic system 12 can include at least one of a line CCD (charge coupled device), a CID (charge injection device) array, and a light dispersing device such as a grating or a prism. Additionally, diagnostic system 12 can include a monochromator (e.g., grating/detector system) for measuring light at a given wavelength, or a spectrometer (e.g., with a rotating grating) for measuring the light spectrum such as, for example, the device described in U.S. Pat. No. 5,888,337.

The diagnostic system 12 can include a high resolution Optical Emission Spectroscopy (OES) sensor such as from Peak Sensor Systems, or Verity Instruments, Inc. Such an OES sensor has a broad spectrum that spans the ultraviolet (UV), visible (VIS), and near infrared (NIR) light spectrums. The resolution is approximately 1.4 Angstroms, that is, the sensor is capable of collecting 5550 wavelengths from 240 to 1000 nm. For example, the OES sensor can be equipped with high sensitivity miniature fiber optic UV-VIS-NIR spectrometers which are, in turn, integrated with 2048 pixel linear CCD arrays.

The spectrometers receive light transmitted through single and bundled optical fibers, where the light output from the optical fibers is dispersed across the line CCD array using a fixed grating. Similar to the configuration described above, light passing through an optical vacuum window is focused onto the input end of the optical fibers via a convex spherical lens. Three spectrometers, each specifically tuned for a given spectral range (UV, VIS and NIR), form a sensor for a process chamber. Each spectrometer includes an independent A/D converter. And lastly, depending upon the sensor utilization, a full emission spectrum can be recorded every 0.1 to 1.0 seconds.

Figure 4:
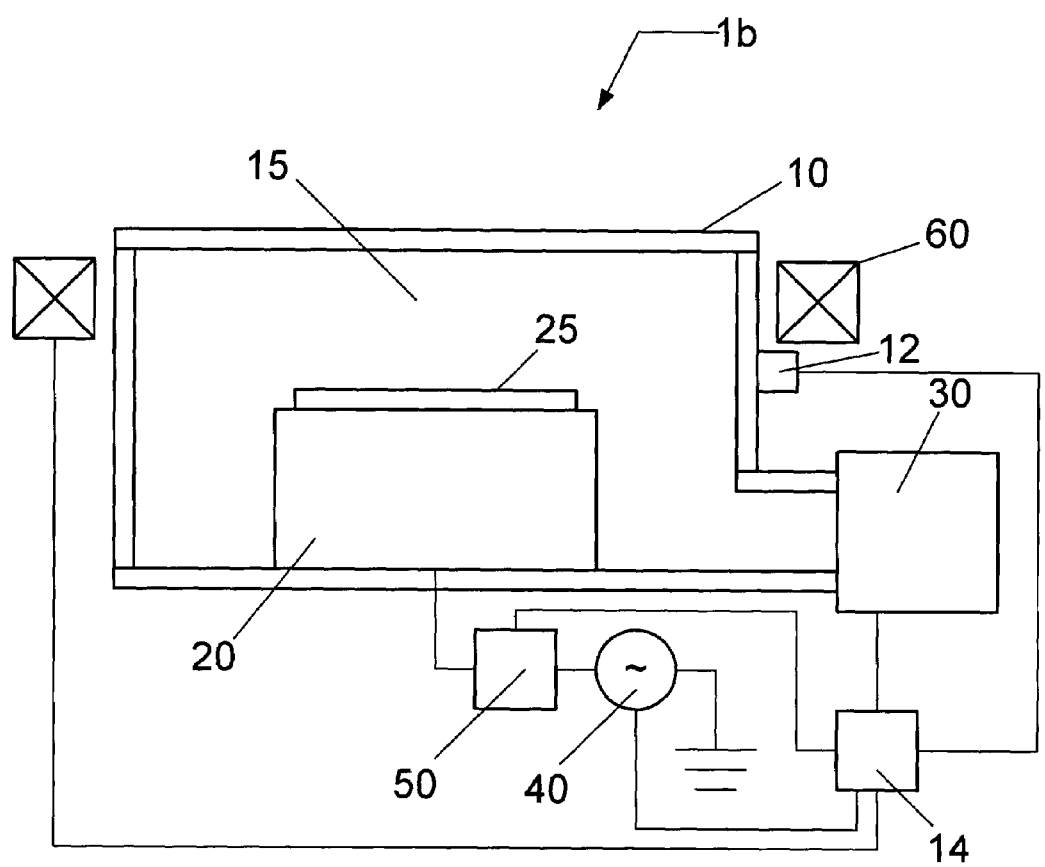
FIG. 4 shows a schematic diagram of a plasma processing system according to another embodiment of the present invention.

In the embodiment shown in FIG. 4, the plasma processing system 1b can, for example, be similar to the embodiment of FIG. 2 or 3 and further comprise either a stationary, or mechanically or electrically rotating magnetic field system 60, in order to potentially increase plasma density and/or improve plasma processing uniformity, in addition to those components described with reference to FIG. 2 and FIG. 3. Moreover, controller 14 can be coupled to magnetic field system 60 in order to regulate the speed of rotation and field strength. The design and implementation of a rotating magnetic field is well known to those skilled in the art.

Figure 5:
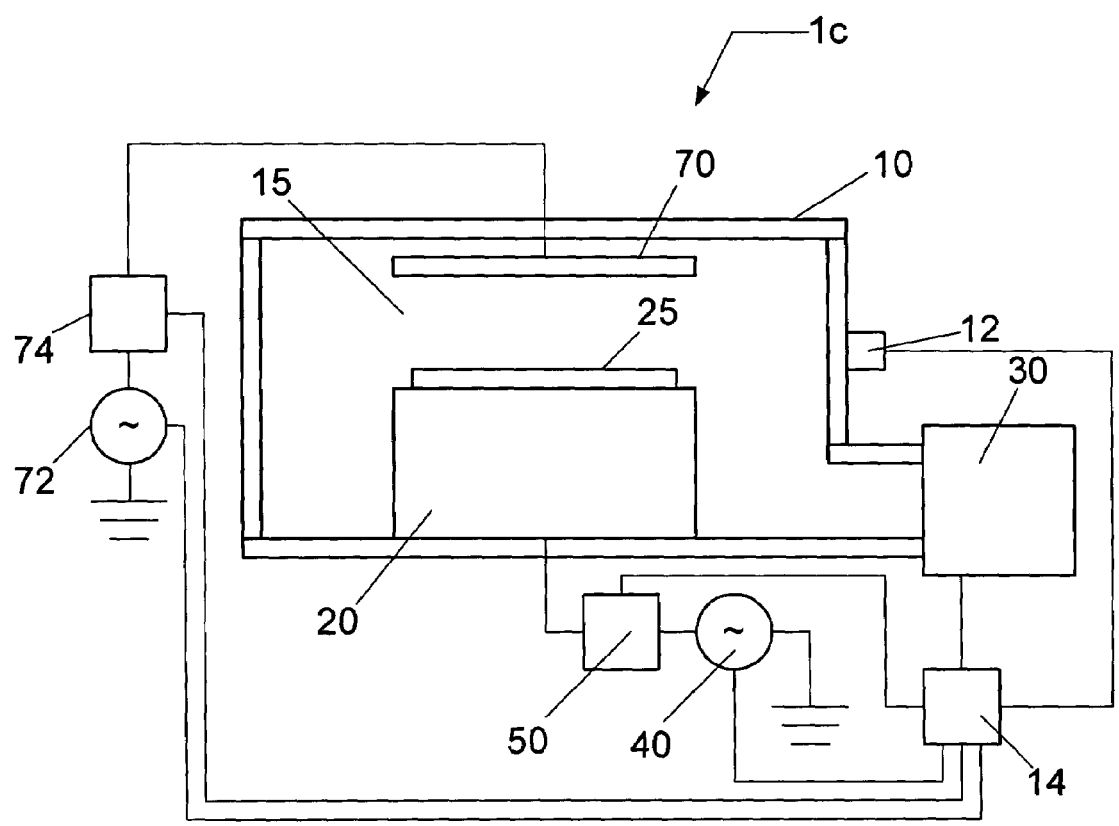
FIG. 5 shows a schematic diagram of a plasma processing system according to another embodiment of the present invention.

In the embodiment shown in FIG. 5, the plasma processing system 1c can, for example, be similar to the embodiment of FIG. 2 or FIG. 3, and can further comprise an upper electrode 70 to which RF power can be coupled from RF generator 72 through impedance match network 74. A typical frequency for the application of RF power to the upper electrode can range from 0.1 MHz to 200 MHz. Additionally, a typical frequency for the application of power to the lower electrode can range from 0.1 MHz to 100 MHz. Moreover, controller 14 is coupled to RF generator 72 and impedance match network 74 in order to control the application of RF power to upper electrode 70. The design and implementation of an upper electrode is well known to those skilled in the art.

Figure 6:
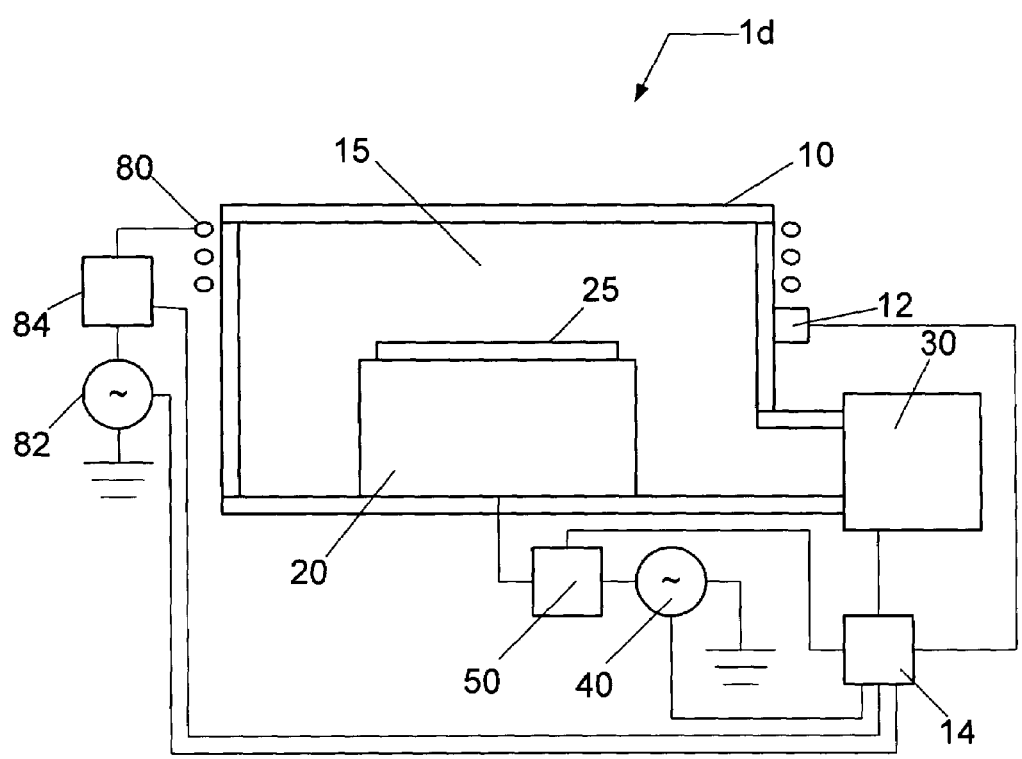
FIG. 6 shows a schematic diagram of a plasma processing system according to another embodiment of the present invention.

In the embodiment shown in FIG. 6, the plasma processing system 1d can, for example, be similar to the embodiments of FIGS. 2 and 3, and can further comprise an inductive coil 80 to which RF power is coupled via RF generator 82 through impedance match network 84. RF power is inductively coupled from inductive coil 80 through a dielectric window (not shown) to plasma processing region 15. A typical frequency for the application of RF power to the inductive coil 80 can range from 10 MHz to 100 MHz. Similarly, a typical frequency for the application of power to the chuck electrode can range from 0.1 MHz to 100 MHz. In addition, a slotted Faraday shield (not shown) can be employed to reduce capacitive coupling between the inductive coil 80 and plasma. Moreover, controller 14 is coupled to RF generator 82 and impedance match network 84 in order to control the application of power to inductive coil 80.

In an alternate embodiment, inductive coil 80 can be a "spiral" coil or "pancake" coil in communication with the plasma processing region 15 from above as in a transformer coupled plasma (TCP) reactor. The design and implementation of an inductively coupled plasma (ICP) source, or transformer coupled plasma (TCP) source, is well known to those skilled in the art.

Alternately, the plasma can be formed using electron cyclotron resonance (ECR). In yet another embodiment, the plasma is formed from the launching of a Helicon wave. In yet another embodiment, the plasma is formed from a propagating surface wave. Each plasma source described above is well known to those skilled in the art.

In the following discussion, a method of etching an organic ARC layer utilizing a plasma processing device is presented. For example, the plasma processing device can comprise various elements, such as described in FIGS. 2 through 6, and combinations thereof.

In an embodiment, the method of etching an organic ARC layer comprises $NH_3$ and a hydrocarbon gas such as at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, $C_6H_{12}$, or the like. For example, a process parameter space can comprise a chamber pressure of 20 to 1000 mTorr, an $NH_3$ process gas flow rate ranging from 50 to 1000 sccm, a hydrocarbon process gas flow rate ranging from 5 to 100 sccm, an upper electrode (e.g., element 70 in FIG. 5) RF bias ranging from 500 to 2000 W, and a lower electrode (e.g., element 20 in FIG. 5) RF bias ranging from 10 to 500 W. Also, the upper electrode bias frequency can range from 0.1 MHz to 200 MHz, e.g., 60 MHz. In addition, the lower electrode bias frequency can range from 0.1 MHz to 100 MHz, e.g., 2 MHz.

In an example, a method of etching an organic ARC layer utilizing a plasma processing device such as the one described in FIG. 5 is presented. However, the methods discussed are not to be limited in scope by this exemplary presentation. Table I presents the critical dimensions of a feature etched in an organic ARC layer utilizing the following exemplary process recipe: Chamber pressure=100 mTorr; Upper electrode RF power=1200 W; Lower electrode RF power=100 W; Process gas flow rate $NH_3/C_2H_4$=450/50 sccm; a 55 mm electrode spacing between the lower surface of electrode 70 (see FIG. 5) and the upper surface of substrate 25 on substrate holder 20; Lower electrode temperature (e.g., substrate holder 20 in FIG. 5)=20C; Upper electrode temperature (e.g., electrode 70 in FIG. 5)=60C; Chamber wall temperature=50C; Backside helium pressure Center/Edge=10/35 Torr; and an etch time of 180 seconds.

TABLE I

| (Photoresist - PR; Critical dimension - CD). | | |
| --- | --- | --- |
| $NH_3/C_2H_4$ | CENTER | EDGE |
| Top PR Remaining | 478 nm | 493 nm |
| Bottom CD/bias - MC | 154/6 nm | 147/−3 nm |
| Bottom CD/bias - CA | 138/−5 nm | 134/−9 nm |

Table I reports results (for both metal contacts (MC) as well as contacts (CA)) such as thickness of the remaining photoresist following the ARC layer etch, top and bottom critical dimensions for the ARC feature, and the critical dimension bias, wherein the bias indicates the change in CD from top to bottom (i.e. negative bias indicates a CD reduction, and positive bias indicates a CD increase). Additionally, the data is reported at center and edge. The data demonstrates the success of the process in maintaining the CD as well as the potential for reducing the CD.

In an alternate embodiment, the process chemistry can further comprise Helium (He). The introduction of Helium to the process can relieve feature side-wall roughness.

In general, the etch time can be determined using design of experiment (DOE) techniques; however, it can also be determined using endpoint detection. One possible method of endpoint detection is to monitor a portion of the emitted light spectrum from the plasma region that indicates when a change in plasma chemistry occurs due to substantially near completion of the ARC layer etching and contact with the underlying material film. For example, portions of the spectrum that indicate such changes comprise wavelengths of 387.2 nm (carbon-nitrogen (CN)), and can be measured using optical emission spectroscopy (OES). After emission levels corresponding to those frequencies cross a specified threshold (e.g., drop to substantially zero or increase above a particular level), an endpoint can be considered to be complete. Other wavelengths that provide endpoint information can also be used. Furthermore, the etch time can be extended to include a period of over-etch, wherein the over-etch period constitutes a fraction (i.e. 1 to 100%) of the time between initiation of the etch process and the time associated with endpoint detection.

Figure 7:
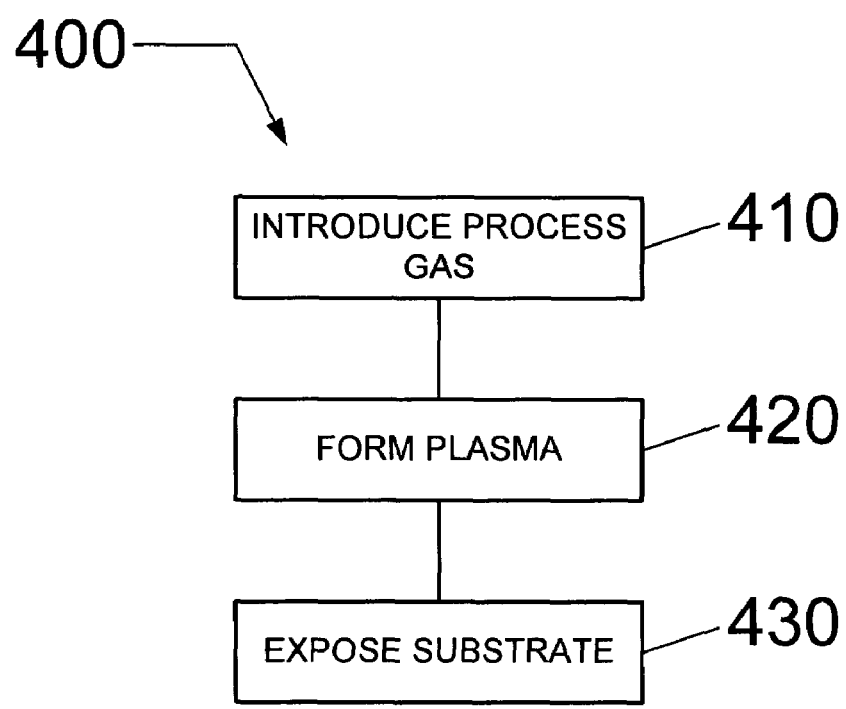
FIG. 7 presents a method of etching an anti-reflective coating (ARC) layer on a substrate in a plasma processing system according to an embodiment of the present invention.

FIG. 7 presents a flow chart of a method for etching an anti-reflective coating (ARC) layer on a substrate in a plasma processing system according to an embodiment of the present invention. Procedure 400 begins in 410 in which a process gas is introduced to the plasma processing system, wherein the process gas comprises ammonia ($NH_3$) containing gas, and a passivation gas. For example, the passivation gas can comprise a hydrocarbon gas such as at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, and $C_6H_{12}$. Alternately, the process gas can further comprise helium (He).

In 420, a plasma is formed in the plasma processing system from the process gas using, for example, any one of the systems described in FIGS. 2 through 6, or combinations thereof.

In 430, the substrate comprising the ARC layer is exposed to the plasma formed in 420. After a first period of time, procedure 400 ends. For example, the first period of time during which the substrate with the ARC layer is exposed to the plasma is generally dictated by the time required to etch the ARC layer, or the time required to transfer a photoresist pattern to the ARC layer. In general, the first period of time required to transfer a photoresist pattern through the thickness of the ARC layer is pre-determined. Alternately, the first period of time can be further augmented by a second period of time, or an over-etch time period. As described above, the over-etch time can comprise a fraction of time, such as 1 to 100%, of the first period of time, and this over-etch period can comprise an extension of etching beyond the detection of endpoint.

Figure 8:
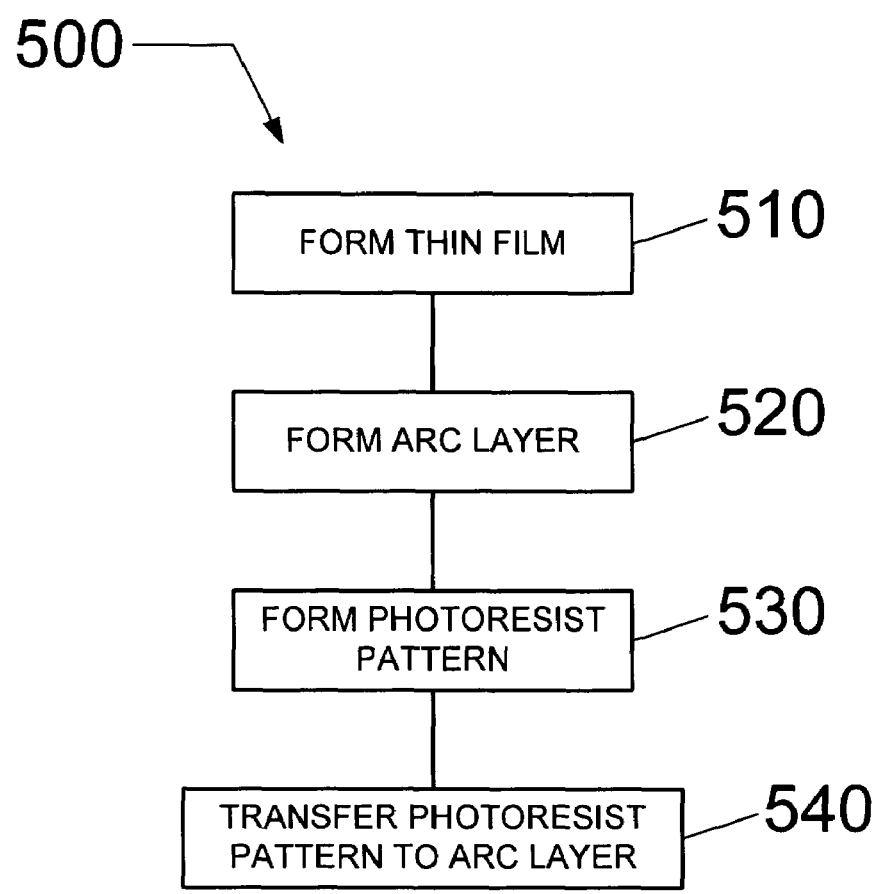
FIG. 8 presents a method of forming a bilayer mask for etching a thin film on a substrate according to another embodiment of the present invention.

FIG. 8 presents a method for forming a bilayer mask for etching a thin film on a substrate in a plasma processing system according to another embodiment of the present invention. The method is illustrated in a flowchart 500 beginning in 510 with forming the thin film on the substrate. The thin film can comprise an oxide layer, such as silicon dioxide ($SiO_2$), and it can be formed by a variety of processes including chemical vapor deposition (CVD).

In 520, an anti-reflective coating (ARC) layer is formed on the substrate overlying the thin film. The ARC layer can, for example, be an organic ARC layer that is formed using conventional techniques such as a spin coating system.

In 530, a photoresist pattern is formed on the substrate overlying the ARC layer. The photoresist film can be formed using conventional techniques, such as a photoresist spin coating system. The pattern can be formed within the photoresist film by using conventional techniques such as a stepping micro-lithography system, and a developing solvent.

In 540, the photoresist pattern is transferred to the ARC layer in order to form the bilayer mask. The pattern transfer is accomplished using a dry etching technique, wherein the etch process is performed in a plasma processing system that utilizes a process gas comprising ammonia ($NH_3$) containing gas, and a passivation gas. For example, the passivation gas can comprise a hydrocarbon gas such as at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, and $C_6H_{12}$. Alternately, the process gas, as described above, can further comprise helium (He). Plasma is formed in the plasma processing system from the process gas using, for example, any one of the systems described in FIGS. 2 through 6, and the substrate comprising the ARC layer is exposed to the plasma formed. A first period of time during which the substrate with the ARC layer is exposed to the plasma is generally dictated by the time required to etch the ARC layer, or the time required to transfer a photoresist pattern to the ARC layer. In general, the first period of time required to transfer a photoresist pattern through the thickness of the ARC layer is pre-determined. However, typically, the first period of time is further augmented by a second period of time, or an over-etch time period. As described above, the over-etch time can comprise a fraction of time, such as 1 to 100%, of the first period of time, and this over-etch period can comprise an extension of etching beyond the detection of endpoint.

Figure 9A:
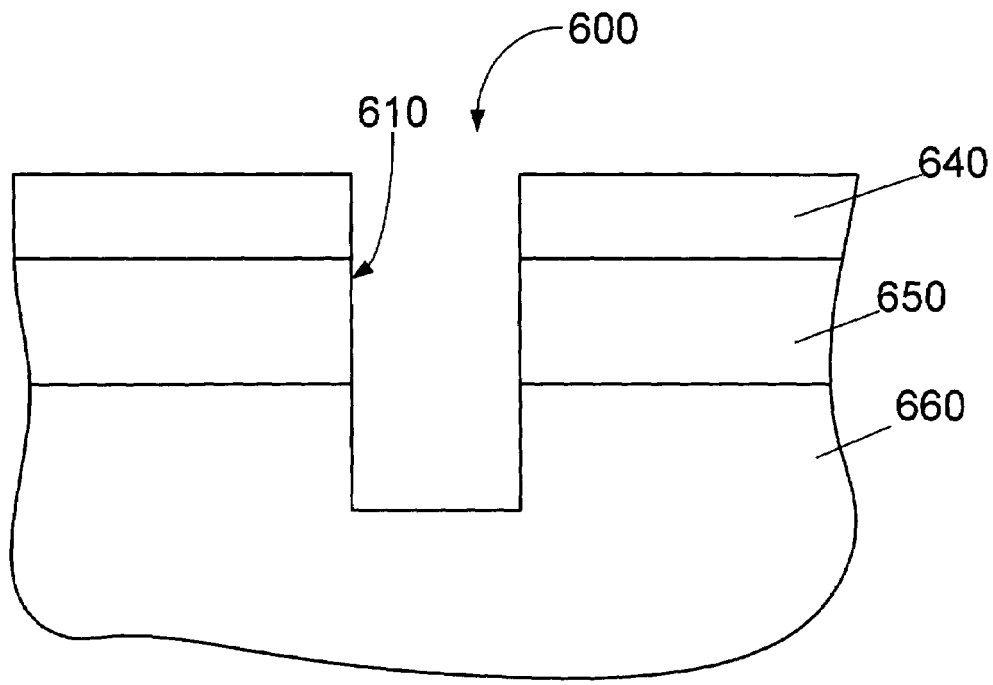
FIGS. 9A and 9B show a schematic representation of a multilayer mask.
Figure 9B:
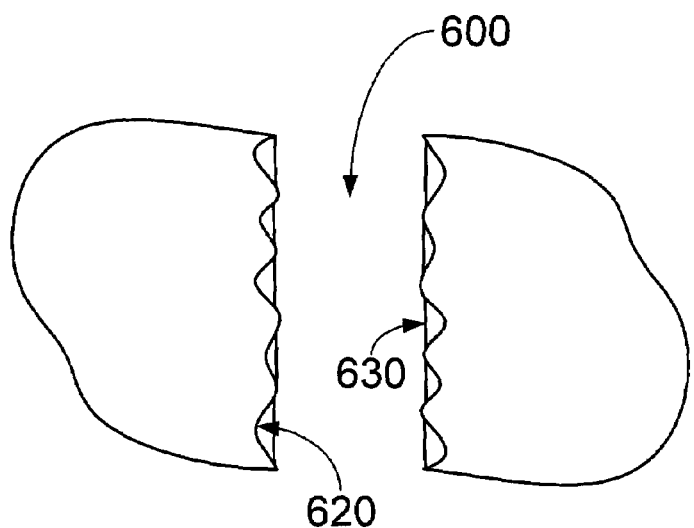

FIGS. 9A and 9B present a side view and a top view of an etched multilayer mask, respectively. Feature 600 comprises sidewalls 610 through light-sensitive layer 640 and ARC layer 650 upon which surface roughness 620 is formed during etching. The passivation gas facilitates the formation of a passivation film 630 to smooth the surface roughness 620 of the etched multilayer mask; see FIG. 9B.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

What is claimed is:

1. A method for etching an anti-reflective coating (ARC) layer on a substrate in a plasma processing system comprising:

introducing a process gas comprising one or more gasses collectively containing ammonia ($NH_3$), and a passivation gas, wherein said passivation gas comprises a hydrocarbon gas and the process gas flow rate ranges from 50 to 1,000 sccm and the passivation gas flow rate ranges from 5 to 100 sccm, forming a plasma from said process gas in said plasma processing system; and exposing said substrate to said plasma, wherein said exposing said substrate to said plasma is performed for a first period of time, and wherein said first period of time corresponds to the time to etch said ARC layer and is extended by a second period of time.

2. The method as recited in claim 1, wherein said passivation gas comprises at least one of $C_2H_4$, $CH_4$, $C_2H_2$, $C_2H_6$, $C_3H_4$, $C_3H_6$, $C_3H_8$, $C_4H_6$, $C_4H_8$, $C_4H_{10}$, $C_5H_8$, $C_5H_{10}$, $C_6H_6$, $C_6H_{10}$, and $C_6H_{12}$.

3. The method as recited in claim 2, wherein said process gas farther comprises helium.

4. The method as recited in claim 1, wherein said first period of time is determined by endpoint detection.

5. The method as recited in claim 4, wherein said endpoint detection comprises optical emission spectroscopy.

6. The method as recited in claim 1, wherein said second period of time is a fraction of said first period of time.

7. A method for etching an anti-reflective coating (ARC) layer on a substrate in a plasma processing system comprising:

introducing a process gas comprising one or more gasses collectively containing ammonia ($NH_3$), and a passivation gas, wherein said passivation gas comprises a hydrocarbon gas and the process gas flow rate ranges from 50 to 1,000 sccm and the passivation gas flow rate ranges from 5 to 100 sccm;

forming a plasma from said process gas in said plasma processing system; and exposing said substrate to said plasma, wherein a ratio of the process gas to the passivation gas is 450/50 sccm.

* * * * *